United States Patent [19]

Aigner

[11] Patent Number: 4,540,402
[45] Date of Patent: Sep. 10, 1985

[54] DOUBLE PERFUSION CATHETER

[76] Inventor: Karl Aigner, Uhlandstr. 5, 6301 Pohlheim, Fed. Rep. of Germany

[21] Appl. No.: 486,680

[22] Filed: Apr. 20, 1983

[30] Foreign Application Priority Data

Apr. 20, 1982 [DE] Fed. Rep. of Germany ....... 3214397

[51] Int. Cl.³ .......................... A61M 1/03; A61M 5/00
[52] U.S. Cl. .......................................... 604/44; 604/8
[58] Field of Search .................................. 604/43–45, 604/272–274, 164; 128/DIG. 3

[56] References Cited

U.S. PATENT DOCUMENTS

| 883,583 | 3/1908 | Stallsmith | 604/43 |
| 2,474,665 | 6/1949 | Guarino | 128/DIG. 3 |
| 3,833,003 | 9/1974 | Taricco | 604/164 X |
| 4,134,402 | 1/1979 | Mahurkar | 604/272 X |
| 4,299,217 | 11/1981 | Sagae et al. | 604/44 |
| 4,405,313 | 9/1983 | Sisley et al. | 604/43 |

Primary Examiner—Dalton L. Truluck
Attorney, Agent, or Firm—Keil & Weinkauf

[57] ABSTRACT

A perfusion catheter, designed as a double catheter which includes a splint catheter (1) and a mounted second catheter tube (3), which is shorter than the splint catheter (1) and which branches off from splint catheter (1). The splint catheter includes an attached shunt tube (2) and at least one lateral opening (4). A solid rod (7) is inserted into the splint catheter (1) from its back end so as to temporarily close the lateral opening(s) (4) and the shunt (2). The catheter is particularly useful for the isolated perfusion of the liver.

10 Claims, 4 Drawing Figures

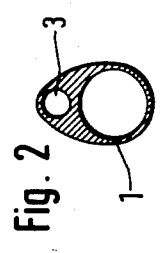
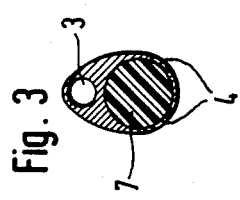
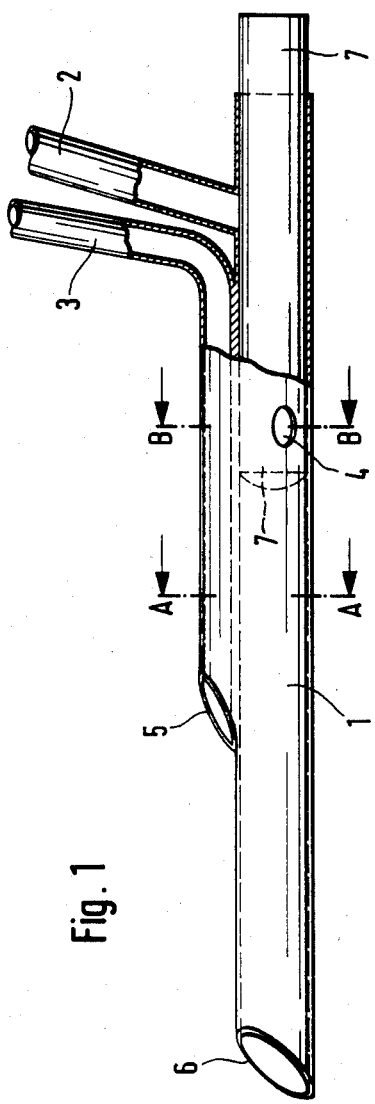
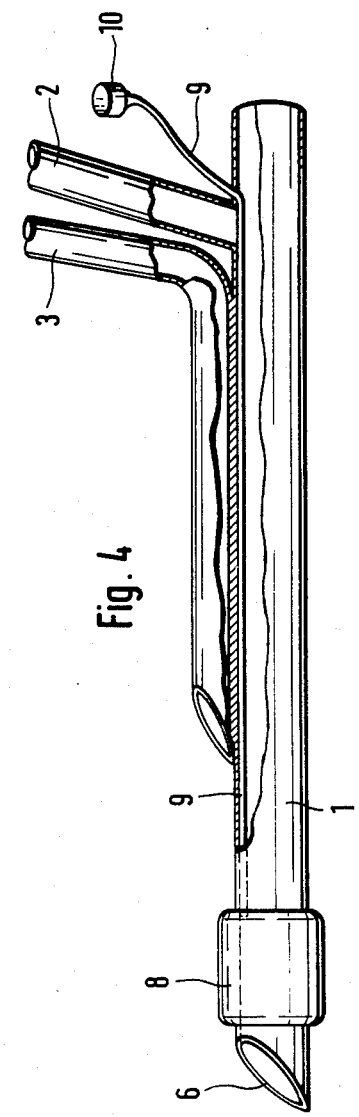

4,540,402

DOUBLE PERFUSION CATHETER

The present invention is directed to a perfusion catheter, to be used particularly for isolated perfusion of the liver in intraarterial chemotherapy.

BACKGROUND OF THE INVENTION

Catheters have long been used for medical purposes and have a variety of applications.

DE-OS No. 30 10 841 describes a double catheter, the catheter tubes of which can be shifted in relation to each other and which can be employed for venipuncture in hemodialysis. The mobility of the individual catheters makes it possible, after insertion into a vessel, to space the inlets or outlets located at the tips of the individual catheters in such a way that the blood returned into the vessel does not reach the area from which it was removed.

DE-OS No. 27 03 087 describes a double capacity catheter for extracorporeal hemodialysis with two separate tubes for the removal and return of blood. The catheter tubes have a coaxial arrangement. At the end not introduced into the blood vessel there is an attachment element for the outer tube. In intraarterial chemotherapy, however, the known catheters have a restricted use, in particular they cannot be used for the isolated perfusion of certain organs or body parts.

The hematogenic metastasis of tumors, particularly from the gastrointestinal region into the liver, occurs by way of the portal vein. For this reason it is desirable to perform isolated perfusion of the tumerous liver by way of the arteria hepatica and the vena portae.

The objective of the present invention is to create a perfusion catheter whose structural design permits isolated perfusion of the liver, without necessitating the interruption of circulation through the vena cava and the vena portae and which permits the isolated withdrawal of blood from the liver during perfusion.

BRIEF SUMMARY OF THE INVENTION

This objective of the invention is achieved by means of a perfusion catheter designed in the form of a double catheter, with a splint catheter and a second mounted catheter that is shorter than the splint catheter, wherein the back end of the second catheter branches off laterally from the splint catheter, wherein at a distance from the back end of the splint catheter there is a shunt tube and wherein at a given distance from the connecting point of this shunt tube there is at least one opening.

BRIEF DESCRIPTION OF THE DRAWING

FIG. 1 is a schematic longitudinal view of the part of the perfusion catheter that is inserted into the main vessel during perfusion.

FIG. 2 is a cross-sectional view of the double catheter along line A—A of FIG. 1.

FIG. 3 is a cross-sectional view of the double catheter along line B—B of FIG. 1, which indicates the position of the lateral openings.

FIG. 4 shows an embodiment of with mounted balloon.

DETAILED DESCRIPTION OF THE INVENTION

In FIG. 1, the splint catheter is marked 1; its front end 6 is introduced into the vessel. Mounted on the splint catheter 1, the second catheter tube 3 is shorter and its end is tapered in such a way that the outer diameter of the double catheter in this area continuously increases. The back end of the second catheter tube runs off to the side from the back part of the splint catheter in the proximity of the shunt tube 2. The shunt tube is positioned at a distance of several cm from the back end of the splint catheter 1. At a certain distance from this connecting point, in the direction of its front end, the splint catheter 1 has a side opening 4. These openings are ideally oval in the longitudinal direction; each is several mm wide and about 10–20 mm, preferably 16 mm. The splint catheter has a length of about 250 mm; its inner diameter is 8–16 mm, preferably 10 mm, and the wall thickness is 1–2 mm. The center of the connecting point is preferably 20 mm from the back end of the catheter tube. The second catheter tube is shorter in form and the front end is located about 80–120 mm behind the front end 6 of the splint catheter. The inner diameter of the second catheter tube can be 4–6 mm. The inner diameter of the shunt tube 2 is 4–6 mm and the wall thicknesses are between 1 and 2 mm.

A closed tube piece or a solid rod 7 is inserted into the splint catheter 1 in order to close the hole 4 during insertion of the double catheter into the vessel. The outer diameter of this part is such that in inserted position 4 it closes the lateral holes, but can easily be drawn out of the splint catheter.

Not shown in FIG. 1 are the parts attached to the shunt tube 2 for producing the temporary portocaval shunt. In addition to a tube connection, these parts comprise an attached hemofilter, to perform ultra-filtration for partial detoxification of the portal blood, and a roller pump to pump the fluid. The tube connection between the ultra-filtration filter and the shunt tube 2 has a length of about 2.5 m. Between the filter and the tube pump or roller pump there is a tube piece with a rubber membrane for the removal of blood. The length of the tube, from the tube pump to the filter, is about 1.5 m and about 3 m of tube connection are necessary to attach the pump to the vena portae. The filter is a conventional ultra-filtration filter, with membrane surfaces of 0.5–1.5 $m^2$, preferably 1 $m^2$; the membranes have an exclusion border at a molecular weight of about 50,000. The ultra-filtrate removed from the actual filter is measured for volume in a calibrated measuring tank, with an accuracy of ±5 ml; near the filter, between the filter and the shunt tube 2, is a tube connecting piece to refeed the drawn-off liquid (the ultra-filtrate) into the tube system in the form of a replacement solution. This replacement solution is a suitable substitution and an outer diameter of about 7 mm; they are produced of suitable materials, preferably from synthetic rubbers or silicon rubber.

FIG. 2 shows a double catheter in a cross-section along line A—A from FIG. 1, and makes clear the arrangement of the two catheter tubes in relation to each other.

FIG. 3 shows the cross-section through the double catheter at another point along line B—B from FIG. 1 and makes clear how the lateral holes 4 are closed by the inserted rod during insertion into the vessel. This cross-section shows an embodiment of the double catheter with two laterally positioned holes 4, which do not face but rather approach each other. FIGS. 2 and 3 show an embodiment of the double catheter with an egg-shaped cross-section and give an approximation of the relative sizes of inner tubes 1 and 3.

FIG. 4 shows the embodiment with mounted balloon 8 on the front end of the splint catheter 1. The feed line 9 for the inflation medium runs along the inside wall of the splint catheter 1 and runs off the side, together with the shunt tube 2, at the back end of the catheter 1. The figure indicates its course through the wall of the splint catheter. It is also possible, however, to lead a portion of the feed line 9 within the shunt tube 2 and to later lead it out of that tube. At the end of the feed line 9 there is a so-called Luer cone to attach the syringes or other feed devices for the inflation medium. The balloon has a length of 1.5–3 cm, ideally 2 cm. Its distance from the point at which the second catheter tube 3 branches off to the point at which the shunt tube 2 separates from the splint catheter 1 is 15–18 cm, preferably 17 cm. The balloon can be enlarged within the vessel until it has an outer diameter such that it lies closely against the inner wall of the vessel. Increasing the outer diameter of the splint catheter 1 by 5–10 mm by means of the balloon is generally sufficient. Materials generally used for balloon catheters can be used for the balloon.

The invention catheter has the form of a double capacity catheter or a double catheter. The large capacity portion serves to splint the main vessel, which conducts the blood from the lower extremities and the kidneys to the right chamber of the heart. A second, shorter, mounted catheter tube with a smaller diameter serves to drain the venous liver blood during perfusion; it branches off in the vicinity of the back end of the splinted catheter and is attached to a heart-lung machine by means of a tube attachment. The splint catheter displays one or two holes at a given point on its side, through which the venous blood of the vena renalis can enter the splint catheter placed in the vena cava during perfusion. At a given distance from the opening(s), which ideally are oval along the longitudinal axis of the catheter, the splint catheter displays a shunt tube for attaching an ultra-filtration filter and a pump, through which blood, flowing from the vena portae (which is clamped as it approaches the liver) during perfusion, is introduced, by means of a temporary, portocaval shunt, into the splint catheter and thus into the vena cava. Thus shunt contains a roller pump and an ultra-filtration filter for the partial detoxification of the portal blood. Thus, the splint catheter displays a front opening, a back opening, one or two lateral openings, and a shunt; mounted on the thicker splint catheter tube is a second, shorter catheter tube, which runs off to the side in the immediate area of the shunt. In its front portion the double catheter displays only one tube; in the middle portion it displays two parallel tubes, and at the back end only one tube, with a shunt at a certain distance from the back end. The front end of the splint catheter is tapered to facilitate its introduction into the blood vessel. The end of the second catheter tube is tapered, so that the catheter has a continuously increasing outer diameter as it is transformed into a double tube. It is of crucial important that this transition is a smooth one and that there will be no edges, so as to facilitate the introduction of the double tube portion into the vessel. The tapered end of the second, laterally mounted catheter tube preferably displays one or two laterally positioned openings so as to prevent the formation of a front edge. The cross-section of the double catheter tube is oval or egg-shaped. At the front end the cross-section of the splint catheter tube is preferably circular in shape. The inner diameter of the splint catheter is preferably larger than the inner diameter of the second catheter tube. The second catheter tube runs off laterally from the splint catheter at a point near the connection of the shunt tube, preferably immediately at the connection.

At a distance from the end of the second, mounted catheter tube the splint catheter tube displays one or two openings, which may face each other or may be placed diagonally in succession on the side turned away from the second catheter tube. The preferred shape of the openings is oval, with the longitudinal side lying on the longitudinal axis of the splint catheter. The center of the openings in the splint catheter is at a certain distance from the midpoint of the connection point for the shunt tube. The distance can be 40–60 mm, preferably 50 mm. The length of the oval openings is between 10 and 20 mm, preferably 16 mm.

So that the lateral openings in the back portion of the splint catheter can be temporarily closed when the catheter is introduced into the body, there is a closed tube piece in the splint catheter, or a rod of solid material, whose outer diameter is somewhat smaller than the inner diameter of the splint catheter. This part has a length such that, when in inserted position, it covers the side holes and projects beyond the back end of the catheter, making it possible to draw it out of the catheter as soon as the catheter is introduced far enough into the vessel for the holes to be within the blood vessel.

Attached to the shunt tube of the perfusion catheters by means of a tube connection is an ultra-filtration filter, which in turn is attached to the pressure side of a pump, so as to create the temporary portocaval shunt of the vena portae with the vena cava by means of the double catheter positioned in the vena cava during perfusion.

The perfusion catheter can be produced from the materials usually used to manufacture catheters. These materials are neutral toward body fluids; they can be sterilized without difficulty and are sufficiently elastic, but at the same, sufficiently stiff and solid, to be introduced into blood vessels. Suitable materials are polyolefines, polyfluoridated hydrocarbon polymers, synthetic rubbers, and the like; silicon rubber is a preferred material.

During application the splint catheter is inserted over its entire length in the vena cava. By ligating the vessel from the outside the needed, separated spaces are created, as in the outward seal. Since making the ligature around the point of the splint catheter is often difficult due to the close proximity of the heart, a preferred embodiment of the invention displays an inflatable balloon in the area of the catheter point; the balloon is mounted from the outside and can be blown up by means of a feed line, thus creating a seal within the vessel and making the external ligature unnecessary.

Certain of the preferred embodiments of the catheter are described in the dependent claims described on the basis of the illustrations.

LIST OF REFERENCE NUMERALS 1. splint catheter, cavacatheter
2. shunt tube, shunt
3. second catheter tube
4. lateral opening in the splint catheter
5. front end of the second catheter tube
6. front end of the splint catheter
7. closed tube or solid rod
8. balloon
9. feed line
10. Luer cone

I claim:

1. A double perfusion catheter for insertion, over its entire length, in the vena cava during isolated perfusion of the liver, said catheter comprising two individual tubes extending generally in parallel relationship and being solidly attached to each other, namely a first tube (1) in the form of a splint catheter tube, and a second tube (3) carried by, and having a shorter length and a smaller diameter than, said first tube (1), said first tube (1) having a rear opening, a shunt tube (2) laterally branching off from said first tube (1) at a point spaced forwardly from said rear opening, a tapered front opening (6), and at least one lateral opening (4) on the side of said first tube (1) generally opposite the side on which said second tube (3) is carried, said second tube (3) having a tapered front opening (5) at a point rearwardly of the front opening of said first tube (1), and having a rear portion which is open at its end and extends laterally away from the first-mentioned side of said first tube (1), and said lateral opening(s) (4) in said first tube (1) being located at a distance of from 40 to 60 mm from the center of the point of junction of said shunt tube (2) with said first tube (1), such that upon full insertion of said catheter into the vena cava during isolated perfusion of the liver, isolated withdrawal of blood from the liver through said second tube (3) in a rearward direction is made possible while, at the same time, circulation of blood, from said shunt tube (2) as well as from said lateral opening(s) (4), and thence through said first tube (1) in a forward direction remains insured.

2. The catheter of claim 1, wherein the double catheter has an oval or egg-shaped outer cross-section and the inner diameter of the splint catheter tube (1) is larger than the inner diameter of the second catheter tube (3).

3. The catheter of claim 1, wherein the second catheter tube (3) extends laterally away from the splint catheter tube (1) in the vicinity of the junction point for the shunt tube (2).

4. The catheter of claim 1, wherein there are two staggered openings at the end of the second catheter tube (3).

5. The catheter of claim 1, wherein the distance from the center of the opening (4) in the splint catheter tube (1) to the center of the junction point of the shunt tube (2) is 50 mm.

6. The catheter of claim 1, wherein one or two openings (4) in the splint catheter tube are oval in shape and have a length of about 10-20 mm, preferably about 16 mm.

7. The catheter of claim 1, wherein the inner diameter of the splint catheter tube (1) is 8 to 16 mm and the inner diameter of the shunt tube (2) is about 5 mm.

8. The catheter of claim 1, wherein a closed tube piece or rod (7), whose outer diameter is smaller than the inner diameter of the splint catheter tube (1), is placed inside the splint catheter tube through the rear end thereof over a length such that the lateral openings (4) are thereby closed and the end of the rod (7) projects beyond the rear end of the splint catheter tube (1).

9. The catheter of claim 1, wherein the catheter is made of silicon rubber.

10. The catheter of claim 1, wherein the splint catheter tube (1) includes an inflatable balloon (8) at a slight distance from its tapered front end, said balloon having a feed line (9) which runs within the splint catheter tube (1) and, together with the shunt tube (2), branches off laterally at the rear end of the catheter tube (1) and has at its end a connection means in the form of a Luer cone.

* * * * *